United States Patent [19]

Eltoukhy et al.

[11] Patent Number: 5,227,211
[45] Date of Patent: Jul. 13, 1993

[54] MAGNETIC RECORDING DISK MEDIUM COMPRISING A MAGNETIC THIN FILM AND A CARBON OVERCOAT HAVING SURFACE NITROGEN ATOMS, A SPECIFIED CARBON STRUCTURE, AND OXYGEN ATOMS

[75] Inventors: Atef H. Eltoukhy, Saratoga; Yassin Mehmandoust, Berkeley, both of Calif.

[73] Assignee: HMT Technology Corporation, Fremont, Calif.

[21] Appl. No.: 664,932

[22] Filed: Mar. 5, 1991

Related U.S. Application Data

[63] Continuation-in-part of Ser. No. 341,936, Apr. 21, 1989, Pat. No. 5,074,983, which is a continuation-in-part of Ser. No. 341,705, Apr. 21, 1989.

[51] Int. Cl.$^5$ .............................................. G11B 5/00
[52] U.S. Cl. ........................................ 428/64; 428/65; 428/336; 428/408; 428/422; 428/694 BP; 428/900; 428/694 TC; 428/667
[58] Field of Search ............... 428/694, 695, 900, 408, 428/336, 64, 65, 422

[56] References Cited

U.S. PATENT DOCUMENTS

| | | | |
|---|---|---|---|
| 4,664,976 | 5/1987 | Kimora et al. | 428/336 |
| 4,717,622 | 1/1988 | Kurokawa et al. | 428/408 |
| 4,833,031 | 5/1989 | Kurokawa et al. | 428/336 |
| 4,861,662 | 8/1989 | Kobuska | 428/408 |
| 4,960,609 | 10/1990 | Homola et al. | 427/38 |
| 5,013,579 | 5/1991 | Yamazaki | 427/38 |

OTHER PUBLICATIONS

Caporiccio, Gerardo, "A New Series of Lubricants for Magnetic Recording Media From Bifunctional Perfluoropolyethel Derivatives" Lecture at Symposium on Memory and Advanced Recording Technologies San Jose, Calif. 5-8 May 1986.

Primary Examiner—Paul J. Thibodeau
Assistant Examiner—Stevan A. Resan
Attorney, Agent, or Firm—Peter J. Dehlinger

[57] ABSTRACT

A thin film magnetic disc having a carbon overcoat which is characterized by (a) a thickness of less than about 500 Å and (b) surface nitrogen atoms having a nitrogen (1s) electron principle binding energy, as determined by electron spectroscopy for chemical analysis (ESCA), of about 399.4 eV. The nitrogen atoms enhance lubricant adhesion to the overcoat. In a preferred embodiment, the overcoat is formed by sputtering under an argon/hydrocarbon/nitrogen gas atmosphere to produce long resistance-to-erosion times, and high lubricity properties.

8 Claims, 5 Drawing Sheets

MAGNETIC RECORDING DISK MEDIUM COMPRISING A MAGNETIC THIN FILM AND A CARBON OVERCOAT HAVING SURFACE NITROGEN ATOMS, A SPECIFIED CARBON STRUCTURE, AND OXYGEN ATOMS

This application is a continuation-in-part of co-pending U.S. patent application for "Thin-Film Testing Method," Ser. No. 341,936, now U.S. Pat. No. 5,074,983 and "Substrate with Carbon Overcoat," Ser. No. 341,705, pending both filed Apr. 21, 1989.

FIELD OF THE INVENTION

The present invention relates to a carbon overcoat having surface nitrogen atoms which serve to enhance the adhesion of perfluoropolyether lubricants, such as in a thin-film medium, and to a method for producing such an overcoat.

REFERENCES

Craig, S., et al, Thin Solid Films, 97:345 (1982).
Kobayashi, K., et al., Thin Solid Films, 158:233 (1988).
Natarajan, V., et al., J Vac Sci Technology, A3(3):681 (1985).
Research Disclosure RD269061, K. Mason Publications, Ltd., England (1986).
Tsai, H-C., et al., J Vac Sci Technol, A5(6):3287 (1987).
Yolamanchi, R. S., et al., Thin Solid Films, 164:103 (1988).

BACKGROUND OF THE INVENTION

Carbon overcoats are commonly formed on substrates, such as magnetic thin films, in thin-film recording discs. The overcoat functions to protect the underlying magnetic layer from damage and wear caused by repeated contact between the disc and the read-write head used in accessing the disc. For this reason, the carbon overcoat is ideally formed to have a high degree of hardness or erosion-resistance.

In addition, the graphite overcoat is intended to provide lubricating surface properties, to minimize drag on the head and wear on the disc during prolonged head/disc contact. The overcoat therefore ideally provides a low-friction surface. The lubricity of a hard carbon overcoat on a disc may be enhanced by covering the overcoat with a thin liquid layer of a stable fluid lubricant, such as a perfluoropolyether lubricant. The optimum friction reduction may be achieved with a liquid layer of perfluoropolyether of about 15–30 Å or higher.

A variety of methods have been used heretofore for forming carbon overcoats on a thin-film magnetic disc (Tsai). In one method, known as RF plasma or glow discharge, an RF source is used to decompose a hydrocarbon gas, producing a carbonaceous plasma whose carbon particles are deposited on a thin-film substrate to form the carbon overcoat (e.g., Natarajan; Yolamanchi; and Kobayashi). The RF discharge method is relatively slow, and deposition rates and plasma composition are somewhat difficult to control.

Another method which has been used for producing a carbon overcoat involves carbon deposition by sputtering, typically DC magnetron sputtering, in which the ionized gases are directed onto the target by magnetic fields established in the sputtering device. Typically in this method, a graphite substrate is sputtered onto a thin-layer film substrate in a low-pressure argon atmosphere until an overcoat of the desired thickness is reached.

The resulting carbon overcoat has a predominantly graphitic structure with "islands" of diamond-like crystalline clusters with dimensions on the order of about 20 Å. It is, of course, the diamond-like clusters which impart the hardness properties to the overlayer. Although the overcoat formed in this manner has adequate hardness properties, it would be desirable to increase the lubricity of the layer as well, particularly lubricity after initial wear.

The need for increased lubricity is especially great in the inner diameter region of the disc, where the lubricant applied to the overcoat tends to becomes depleted over time due to migration of the liquid material under centrifugal effects, and particularly, in the inner-diameter region which is dedicated to start-stop head contact, where repeated contact with the head further depletes the liquid layer.

The above-cited co-pending patent applications disclose an improved carbon overcoat formed by carbon sputtering under an argon/hydrocarbon gas atmosphere. In accordance with one aspect of the earlier disclosed invention, it was found that sputtering voltage and pressure conditions can be adjusted to maintain hardness of the overcoat, but increase lubricity substantially over that which is achievable by carbon sputtering in the presence of argon gas alone.

It would further be desirable, for enhancing the surface wear properties of a carbon overcoat in a thin-film medium, to increase lubricant adhesion to the overcoat, to reduce loss of lubricant from the overcoat during disc operation.

SUMMARY OF THE INVENTION

It is therefore one general object of the invention to provide a carbon overcoat having an increased adhesion to a lubricant, such as a perfluoropolyether lubricant.

The present invention includes, in one aspect, an article comprising a substrate with a carbon overcoat having surface nitrogen atoms characterized by a nitrogen (1s) electron principle binding energy, as determined by electron spectroscopy for chemical analysis (ESCA), of about 399.4 eV. The overcoat has enhanced adhesion for lubricant, such as a perfluoropolyether lubricant, compared with an overcoat lacking such surface nitrogen atoms.

The overcoat preferably has a thickness less than about 500 Å, and contains at least about 2 atom percent surface nitrogen atoms. In one preferred embodiment, the overcoat has a diamond-like carbon structure, as evidenced by a carbon (1s) principle binding energy of about 284.8 eV, an oxygen (1s) principle binding energy of about 532.5 eV, and an oxygen abundance of no more than about 10 atom percent, as determined by ESCA.

Also disclosed is a thin-film medium composed of a substrate, a magnetic thin film on the substrate, and such enhanced-adhesion carbon overcoat formed on the magnetic thin film. The medium preferably includes a layer of perfluoropolyether lubricant film on the carbon overcoat.

In another aspect, the invention includes a method of producing, on a substrate, a carbon overcoat having surface nitrogen atoms characterized by a nitrogen (1s) electron principle binding energy, as determined by electron spectroscopy for chemical analysis (ESCA), of about 399.4 eV. The overcoat is produced by sputtering carbon from a carbon target onto the substrate, under an atmosphere containing at least 4 mole percent nitrogen gas. In one preferred method, for producing a carbon overcoat having a diamond-like carbon structure, as evidenced by a carbon (1s) principle binding energy of about 284.8 eV, an oxygen (1s) principle binding energy of about 532.5 eV, and an oxygen abundance of no more than about 10 atom percent, the sputtering is carried out under an atmosphere containing 10-50 mole percent hydrogen or hydrocarbon gas, 5-50 mole percent nitrogen gas, and remainder argon gas. The method may further include applying a perfluoropolyether lubricant to the carbon overcoat, to form an adherent lubricant layer on the overcoat.

In still another aspect, the invention includes a method of enhancing adhesion of a perfluoropolyether lubricant to a carbon overcoat. In this method, the overcoat is formed to include at least about 2 atom percent surface nitrogens atoms characterized by a nitrogen (1s) electron principle binding energy, as determined by electron spectroscopy for chemical analysis (ESCA), of about 399.4 eV.

These and other objects and features of the invention will become more fully apparent when the following detailed description of the invention is read in conjunction with the accompanying drawings.

DETAILED DESCRIPTION OF THE INVENTION

Carbon Overcoat and Preparation

Figure 1:
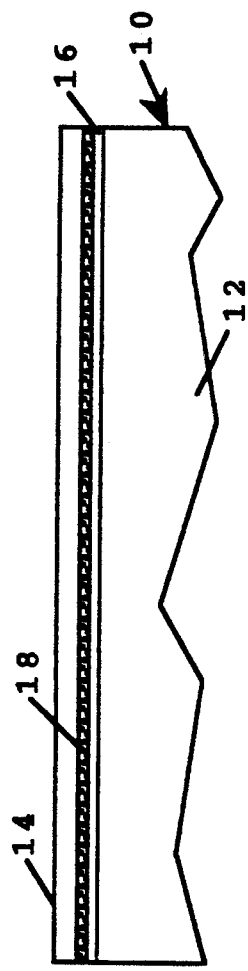
FIG. 1 is a sectional view of a thin-film magnetic disc having a carbon overcoat formed in accordance with the present invention.

FIG. 1 shows in cross section view, a fragmentary portion of an article 10 composed of a base or substrate 12 and a carbon overcoat 14, formed in accordance with the present invention. The overcoat contains surface nitrogen atoms characterized by a nitrogen (1s) electron principle binding energy, as determined by electron spectroscopy for chemical analysis (ESCA), of about 399.4 eV. The overcoat has enhanced adhesion for lubricant, such as a perfluoropolyether lubricant, compared with an overcoat lacking such surface nitrogen atoms, as will be described below.

In the embodiment of the invention shown in FIG. 1, article 10 is a thin-film medium having a rigid disk-like substrate 12, and forming successive thin-film layers over the substrate, a crystalline underlayer 16, a magnetic thin-film layer 18, and overcoat 14.

The substrate may be a textured substrate, such as a conventional surface-coated, textured aluminum substrate of the type used commonly for digital recording medium, or a textured glass or ceramic substrate, such as described in co-owned patent application for "Glass Substrate with Controlled Low-Friction Surface," Ser. No. 475,715, filed Feb. 20, 1990.

The crystalline underlayer is preferably a sputtered chromium underlayer having a thickness between about 300-3,000 Å. The magnetic film layer is preferably a cobalt-based alloy which is formed on the underlayer by sputtering or the like. Exemplary thin-film alloys include cobalt/chromium/nickel, or cobalt/chromium/tantalum/platinum, such as described in co-pending U.S. patent application for "High Coercivity Thin-Film Medium and Method," Ser. No. 567,598, filed Aug. 15, 1990. The just-cited application also discloses suitable sputtering conditions for forming the underlayer and thin-film layer.

Figure 2:
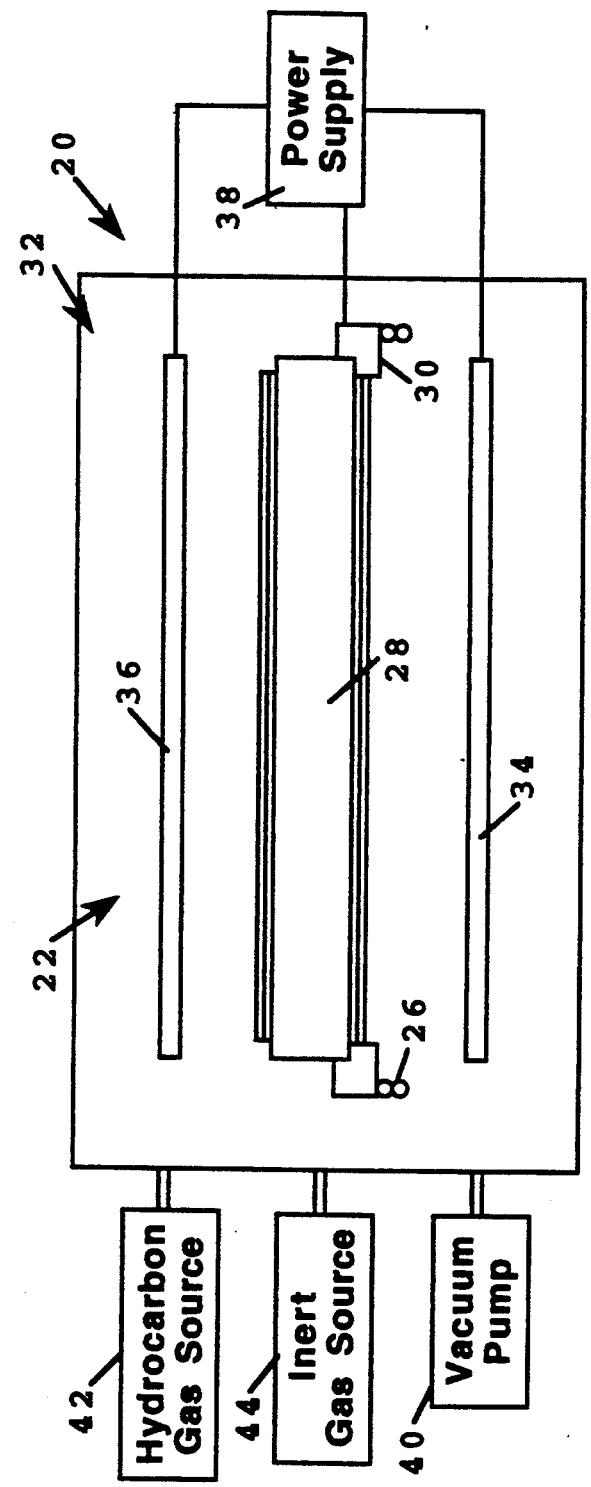
FIG. 2 is a schematic view of sputtering apparatus used in producing the disc shown in FIG. 1.

FIG. 2 shows, in schematic cross-sectional view, a portion of a sputtering apparatus 20 for use in forming the above thin-film medium, including the carbon overcoat. The apparatus includes a vacuum chamber 22 having at least four stations at which heating or sputtering operations occur. Within this chamber is a pair of endless belts, such as belt 26, for carrying substrates, such as substrate 28, through the chamber. The substrates are supported on pallets, such as pallet 30, which is carried through the chamber on the endless belts.

In a sputtering operation, the substrate is carried on the pallet in a downstream direction, from an upstream heating station, through a first sputtering station in which the underlayer is formed, through a second sputtering station in which the thin-film is formed, and through a downstream station 32 in which the carbon overcoat is formed.

Station 32 houses a pair of carbon, i.e., graphite targets 34, 36. The targets are connected to a power supply 38 in the apparatus to achieve a selected target voltage with respect to the disc, as shown. Commercially available graphite targets, such as a POCO ™ target supplied by POCO Graphite, Inc. (Decatur, Tex.) are suitable. The carbon sputtering voltage is typically adjustable between about 400 to 600 volts, giving a power level between about 0.8 and 4 kwatts.

The final pressure in the chamber during a sputtering operation is a selected pressure preferably between about $10^{-3}$ to $10^{-2}$ mBarr. The vacuum pressure is achieved with a conventional low-pressure vacuum pump 40. A sputtering apparatus of the type just described is commercially available, such as from Circuits Processing Apparatus (Fremont, Calif.), Leybald Heraeus (Germany), VACTEK (Boulder, Colo.) or Materials Research Corp (Albany, N.Y.). These systems are all double-sided, in-line, high-throughput machines having two interlocking chambers for loading and unloading.

In the embodiment of the invention shown in FIG. 1, the carbon overcoat is formed by sputtering under a low-pressure, nitrogen-containing atmosphere. In particular, the sputtering atmosphere contains at least 4, and up to 100 mole percent nitrogen gas, i.e., the moles of $N_2$ introduced into the chamber represent between 4 and 100 mole percent of the total gas molecules in the chamber. The low-pressure sputtering atmosphere may also include an inert sputtering gas, such as argon, and a source of hydrogen atoms, such as $H_2$ or a lower alkane gas, such as methane. One preferred gas mixture includes 10-50 mole hydrogen of hydrocarbon gas, 5-50 mole nitrogen, and remainder argon, and preferably 5-10 mole percent $N_2$, 35- 60 mole percent lower alkane , gas, and 30-60 mole percent argon. By way of example, one carbon overcoat whose properties are described below is formed under a low-pressure atmosphere containing 50 mole percent argon, 45 mole percent methane, and 5 mole percent $N_2$.

The nitrogen and other gases are supplied to the chamber from gas sources, such as a nitrogen gas source 42, a hydrocarbon gas source 44, and an argon gas source (not shown). The desired mole percentages of gases in the chamber may be controlled by suitable valving apparatus (not shown) which control the flow rate at which gases are introduced into the chamber. Alternatively, the desired gas may be premixed and admitted to the sputtering chamber from a single mixed-gas source.

In the application of the invention to thin-film media, the carbon overcoat is preferably formed under sputtering conditions which yield a final overcoat thickness of less than about 500 Å, and preferably between about 200-300 Å. The sputtering conditions are also selected, in a preferred embodiment of a thin-film medium, to produce a substantially diamond-like carbon structure, as evidenced by a carbon (1s) principle binding energy of about 284.8 eV, an oxygen (1s) principle binding energy of about 532.5 eV, and an oxygen abundance of no more than about 10 atom percent, as determined by electron spectroscopy for chemical analysis (ESCA), described below.

According to one aspect of the invention, the sputtering conditions may be selected to produce a carbon overcoat having properties of (a) high erosion resistance, (b) high corrosion resistance, (c) good lubricity, and (d) enhanced lubricant adhesion, as will be seen in Section II below.

In producing a carbon overcoat having the above properties, the overcoat sputtering is carried out in an argon, hydrocarbon (or hydrogen) and nitrogen gas mixture, as described above. Considering the voltage and power level parameters, it is observed that voltage drops with increasing amounts of hydrocarbon gas in the chamber, presumably due to the lower impedance of the (ionized) hydrocarbon gas atmosphere. For example, a power supply setting which gives a sputtering voltage of about 600 volts in pure argon gives about 500 volts in 30-50% methane, at the same gas pressure.

The resistance to erosion of a disc overcoat prepared in argon:methane (1:1) at increasing voltage (and power levels) has been examined. Briefly, it was discovered that at a voltage of at least about 80-90% of the "pure argon" voltage—i.e., the optimal level employed for sputtering in a pure inert gas—that greater resistance to erosion was achieved, without loss of lubricity. Thus, at an original voltage of about 600 volts, the voltage would initially drop to about 500 volts, and would be increased up to about 540 volts or greater to restore hardness, where higher voltages are used to attain greater hardness. This same effect has been observed for argon:methane:nitrogen gas mixtures. That is, improved lubricity, without loss of resistance to erosion, can be achieved by increasing sputtering voltage and decreasing sputtering-gas pressure relative to optimal parameter settings for argon gas alone.

Once voltage, power level and gas pressure are adjusted for optimal hardness, at a given gas composition, the percentage of hydrocarbon and nitrogen gas may be further adjusted to further enhance lubricity. The nitrogen-containing carbon substrate may also be formed by other plasma deposition methods, such as plasma chemical vapor deposition. In the latter method, an RF energy source is used to ionize a suitable carbon-containing gas, such as methane, in the presence of nitrogen gas. Deposition of this gas produces the desired nitrogen-containing carbon overcoat.

After formation of the overcoat, the disc is preferably coated with a conventional perfluoropolyether lubricant, such as AN 2001 TM lubricant supplied commercially by Ausimont (Morristown, N.J.). The fluid may be applied conventionally by an endless belt tape device designed to burnish and lubricate a finished disc surface. Alternatively, the finished disc may be dipped in a solution of the lubricant in a suitable solvent. According to the present invention, such lubricant has an enhanced adhesion to the carbon overcoat, forming a durable lubricant film on the overcoat. The greater adhesion characteristics of the overcoat will be seen below.

Carbon Overcoat Properties

Thickness

The carbon overcoat has a thickness less than about 500 Å and preferably about 300 Å, when used as a protective coating in a thin-film magnetic recording medium. For other applications, for example, where the overcoat is used to provide a protective lubricating surface for plastic or metal mechanical parts, the film thickness may be greater (or less) than this specified thickness. The thickness of the overcoat may be controlled, as above, by suitable adjustment in the time-of-travel of the article to be coated through the carbon sputtering station.

Surface Chemical Analysis

Chemical analysis of the surface chemical groups on the overcoat provides information about the atomic composition of surface and the types of bonds formed by the surface atoms. The types of chemical bonds can be determined from the electron binding energy which is characteristic of bond type, such as C—C, C—O, C=O, or C—N. The relative amounts of atoms can be determined by the relative peak areas of the various emission peaks.

Figure 3A:
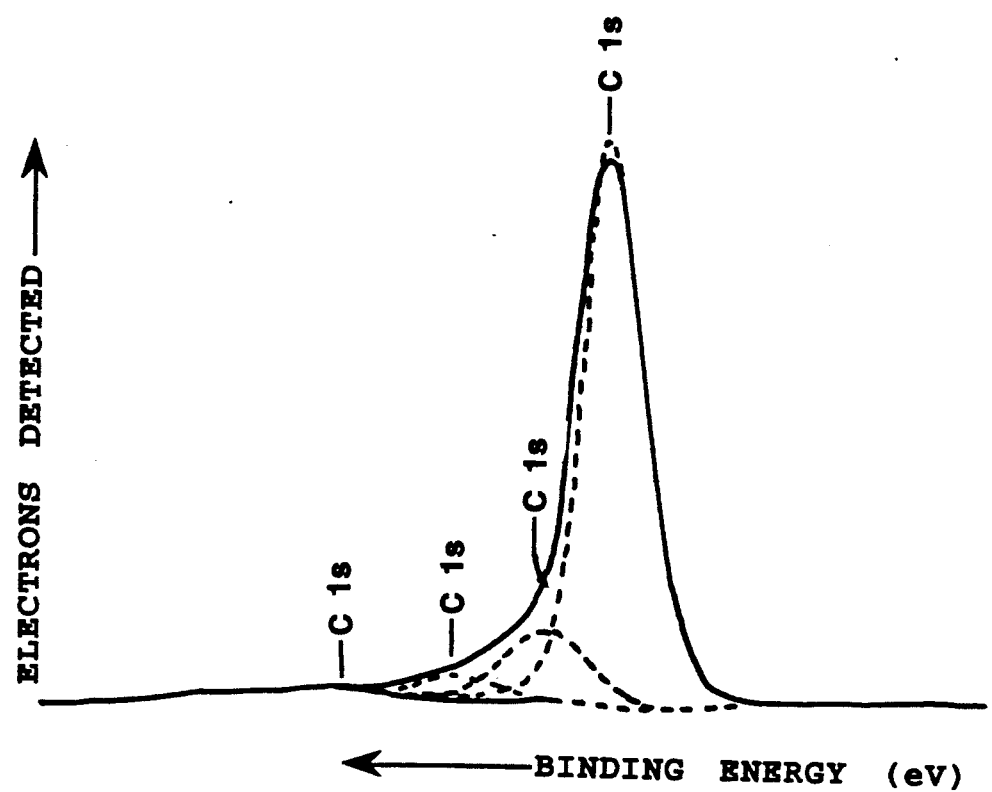
FIGS. 3A-3C are ESCA spectra of carbon overcoats formed by sputtering under an atmosphere of argon alone (3A), argon plus methane (3B), and argon plus methane and nitrogen, in the electron binding energy range between 278 and 298 eV.
Figure 3B:
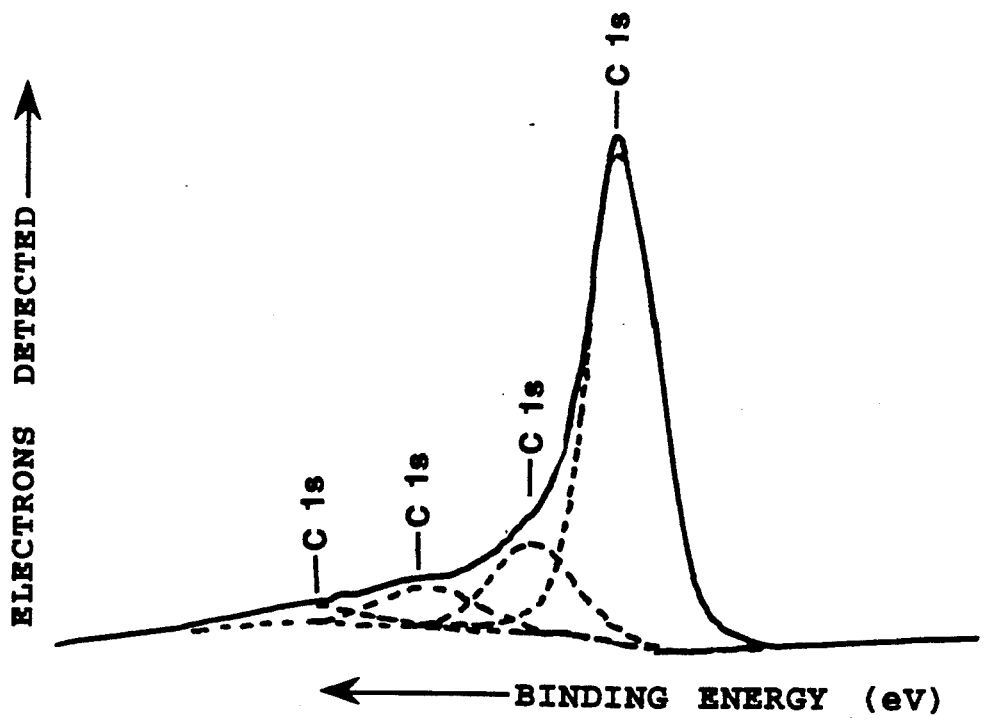
Figure 3C:
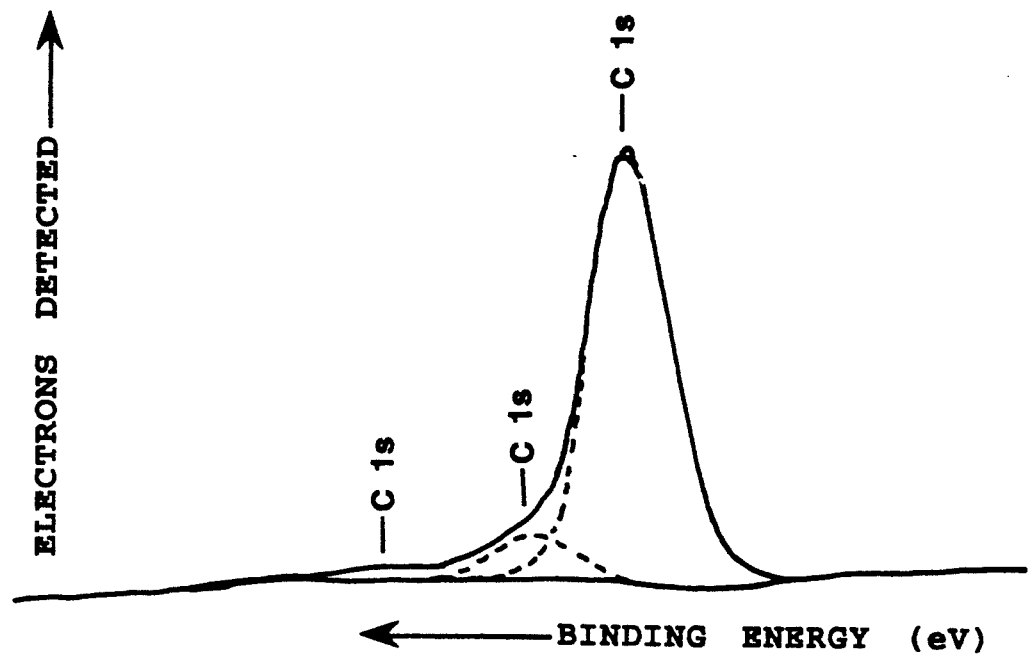
Figure 4:
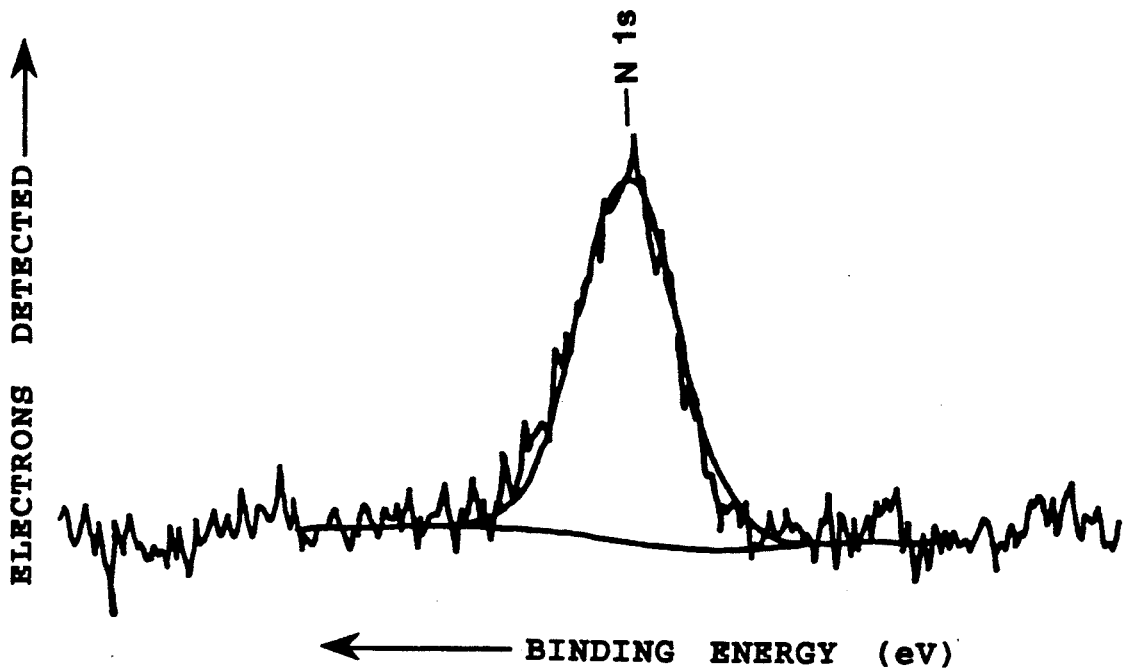
FIG. 4 shows an ESCA spectra of a carbon overcoat formed by sputtering under an atmosphere of argon plus methane and nitrogen, in the electron binding energy range between 390 and 410 eV.

FIGS. 3A-3C show ESCA spectra for carbon overcoats formed under argon (3A), argon:methane, 1:1 (3B)

and argon:methane:nitrogen, 10:9:1 (3C) atmospheres, respectively. The spectra are taken over the spectral energy region from about 278-298 eV. The peaks are related to the 1s carbon electrons in C—C (284.38 eV), C—O (285.97 eV), C=O (287.81 eV), and O—C=O (289.83 eV) chemical groups, as indicated. The relative proportions of each bond type in the three overcoats is shown in Table 1 below.

TABLE 1

| Energy | Bond | Percent (argon) | Percent (argon/methane) | Percent (argon/methane/nitrogen) |
|---|---|---|---|---|
| 284.58 | C—C | 71.5 | 81.7 | 86.9 |
| 285.79 | C—O | 14.8 | 12.9 | 9.5 |
| 287.42 | C=O | 8.7 | 4.2 | 3.7 |
| 289.56 | O—C=O | 5.0 | 1.2 | |

As seen, the relative percentages of oxygen-bound carbon atoms dropped from about 28% for the overcoat made in a argon atmosphere, to about 18% for sputtering in binary gas mixture, to about 13% for sputtering in the ternary, nitrogen containing gas mixture. From the values shown in Table 1, the atomic percentage of each C, O, and N in three carbon overcoats was calculated (Table 2).

TABLE 2

| Spec. | Sample Description | C | O | N |
|---|---|---|---|---|
| | Argon | 85 | 15 | — |
| 1 | Argon/Methane | 90 | 9.7 | — |
| 2 | Argon/Methane/Nitrogen | 88 | 9.1 | 3.1 |
| 3 | Single crystal graphite | 100 | <.1 | — |
| 4 | "Diamond-like" film | 90 | 9.7 | — |

Also shown in Table 2 are relative percentages of carbon and oxygen atoms for a diamond-like carbon film (#4) and for a pure graphite sample (#3). In both cases in which the film was sputtered in the presence of a hydrocarbon gas (samples 1 and 2), a diamond-like film characterized by about 10 atom percent (or less) surface oxygen was observed. In addition, the O(1s) peaks from the two samples (1 and 2) were both single broad peaks with a binding energy roughly 532.5 eV, which is consistent with an amorphous or diamond-like carbon.

Resistance to Erosion

The resistance to erosion was measured by a modified surface texturing device described in the above-cited parent application. Briefly, the device places a pair of rollers covered with an abrasive pad against opposite sides of a rotating disc. The tension on the rollers can be adjusted to achieve a desired surface pressure against the rotating disc. One preferred device of this type is commercially available from Exclusive Design Company (San Mateo, Calif.), Model No. 800 HDF-C. One preferred abrasive surface is a 0.3μ particle size abrasive tape, such as tape No. 511904569 supplied by 3M Corp. (Minneapolis, Minn.).

Resistance to erosion was measured as the time required to wear away a 300 Å overcoat on a disc, when a 0.3μ abrasive tape is applied to the surface of the disc with a force of about 3.5 pounds, and the disc is rotated at 1,800 rpm. These test conditions, although arbitrarily selected, are useful for making quantitative comparisons of overcoat hardness which can be used both for optimizing sputtering conditions and for determining start/stop lifetimes, as above. As measured ny this test, resistance to erosion times were: 4-5 minutes for a carbon overcoat formed as above under a pure argon, and about 8 minutes for carbon overcoats formed under equimolar amounts of argon and methane, and argon:methane:nitrogen (50:45:5). A relatively soft carbon overcoat is worn away in about 2 minutes.

An overcoat having the degree of hardness of 8 minute erosion time, as well as high lubricity, is generally well suited for conventional hard-disc computer storage applications. However, applications which favor softer carbon overcoats are also contemplated.

Lubricity: Hydrophobicity

One measure of lubricity in a carbon overcoat is hydrophobicity. In general, greater hydrophobicity is associated with greater lubricity. This is due to the reduced degree of hydration which occurs on a hydrophobic disc surface, causing less frictional drag at the surface.

One measure of hydrophobicity in a carbon overcoat is the relative percentage of hydrophobic C—C bonds to more hydrophilic bonds, such as C—O and C—N bonds, which have hydrogen bonding capability. The relative percentages of these bond types seen in Table 1 indicate that the carbon overcoats formed under a methane or methane/nitrogen atmosphere, in accordance with the present invention, are more hydrophobic than one formed under a pure argon atmosphere. These overcoats are therefore expected to have greater lubricity, consistent with other physical characteristics noted below.

One direct measure of hydrophobicity is provided by a bead angle test. Here a drop of water is placed on the upper surface of a carbon overcoat (no lubricant layer), and the disc is raised above horizontal to an angle at which the bead first begins to glide on the surface, i.e., slide down the surface. The bead angle in the overcoats formed under argon/methane, or argon/methane/nitrogen were significantly higher than the bead angle of carbon overcoat formed under a pure nitrogen atmosphere, consistent with the atomic composition data from the ESCA studies.

Lubricity: Coefficient of Friction

Another measure of overcoat lubricity is the coefficient of friction, as measured with a standard read/write head. The dynamic coefficient is measured on a disc rotating at a speed of 1 rpm, and the static coefficient, from a stationary disc position.

Figure 7:
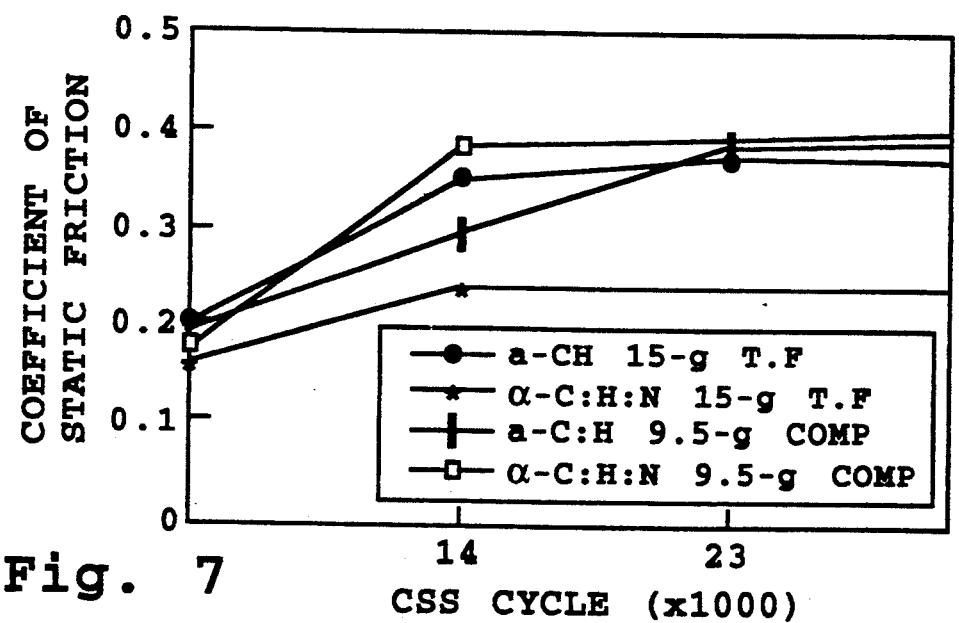
FIG. 7 plots the coefficient of static friction, as a function of start-stop cycles, measured by a 15 g thin-film head (dot and * symbols) or 9.5 g composite head (+ and open rectangle symbols) on a lubricated carbon overcoat formed by sputtering under an argon/methane atmosphere (dot and + symbols) or an argon/methane/nitrogen atmosphere (* and open rectangle symbols)

To measure static and dynamic coefficient of friction after extended start/stop cycles, a disc coated with a perfluoropolyether lubricant (AN 2001) was subjected to 14,000 and 23,000 start/stop cycles, and tested for static coefficient. The results in FIG. 7 show measured static coefficients of friction measured with a 15 g thin-film (T.F.) titanium head on an overcoat formed under an argon/methane (1:1) atmosphere (solid circles) or an argon/methane/nitrogen (10:9:1) atmosphere (*). The nitrogen-containing overcoat showed an increase in static coefficient of less than 0.1 after 23,000 start/stop cycles, compared with an increase of about 0.18 for the non-nitrogen-containing overcoat. For 23,000 start/stop cycles using a 9.5 g composite head, the increase in static coefficient of friction was nearly the same in both overcoats (open rectangle vs. vertical mark). As will be seen below, the increased stability of the nitrogen-containing overcoat to start-stop cycles is likely due to enhanced adhesion of lubricant to the overcoat.

For comparison, similar studies conducting in support of the present invention gave static coefficient of friction values of to 0.6–0.7 after 20,000 start/stop cycles for a carbon overcoat formed under a pure argon atmosphere.

Enhanced Lubricant Adhesion

According to one aspect of the invention, it has been discovered that nitrogen atoms, in a bonding state characterized by a nitrogen (1s) electron principle binding energy of about 399.4 eV, show enhanced lubricant adhesion when compared with the a carbon overcoat having a similar molecular structure but substantially lacking nitrogen atoms.

Figure 5:
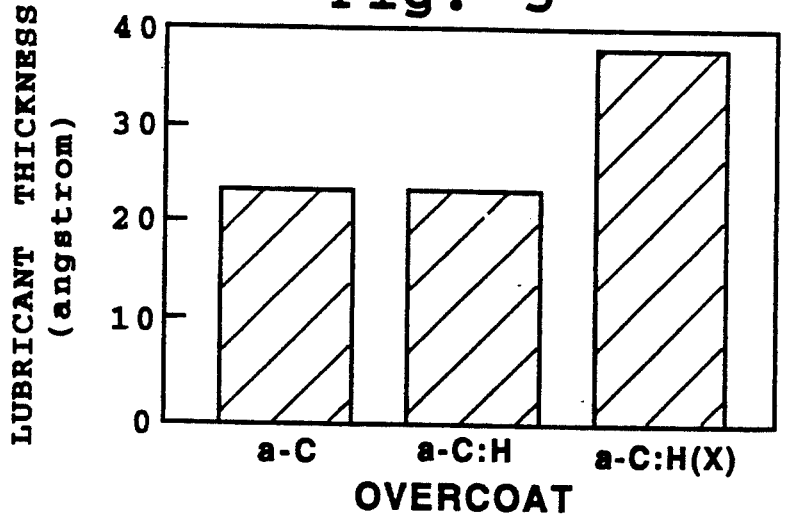
FIG. 5 is a bar graph showing the thickness of perfluoropolyether lubricant added to a carbon overcoat formed by sputtering under pure argon (a-C), argon and methane (a-C:H), and argon, methane, and nitrogen (a-C:H:N)

In particular, it has been found that polyfluorocarbon lubricants, such as perfluoropolyether lubricants, have a significantly greater adhesion to the surface of nitrogen-containing carbon overcoats. One measure of lubricant adhesion is the thickness of a lubricant layer applied to a carbon overcoat. FIG. 5 shows the thickness of lubricant layer applied to carbon overcoats formed by sputtering, as above, under pure argon (a-C), argon/methane (a-C:H), and argon/methane/nitrogen (a-C:H:N). The lubricant layer was applied by dipping a disc into a solution of perfluoropolyether solution, according to standard procedure. The thickness of the lubricant layer was measured by Fourier Transfer I.R. (FTIR) using a commercial FTIR device from Nicolet (Fremont, Calif.). As seen, both of the overcoats formed in the absence of nitrogen absorbed a lubricant layer having a 20–25 Å thickness. This contrasts with the nitrogen-containing overcoat, which has a thickness of about 35–40 Å.

In accordance with a preferred embodiment of the invention, the lubricant is applied to a final lubricant layer of between about 20–40 Å. Lubricant layers at the lower end of this range can be achieved conventionally by dipping the disc in a lower concentration perfluoropolyether solution, or by a further burnishing finishing step, according to standard methods.

Figure 6A:
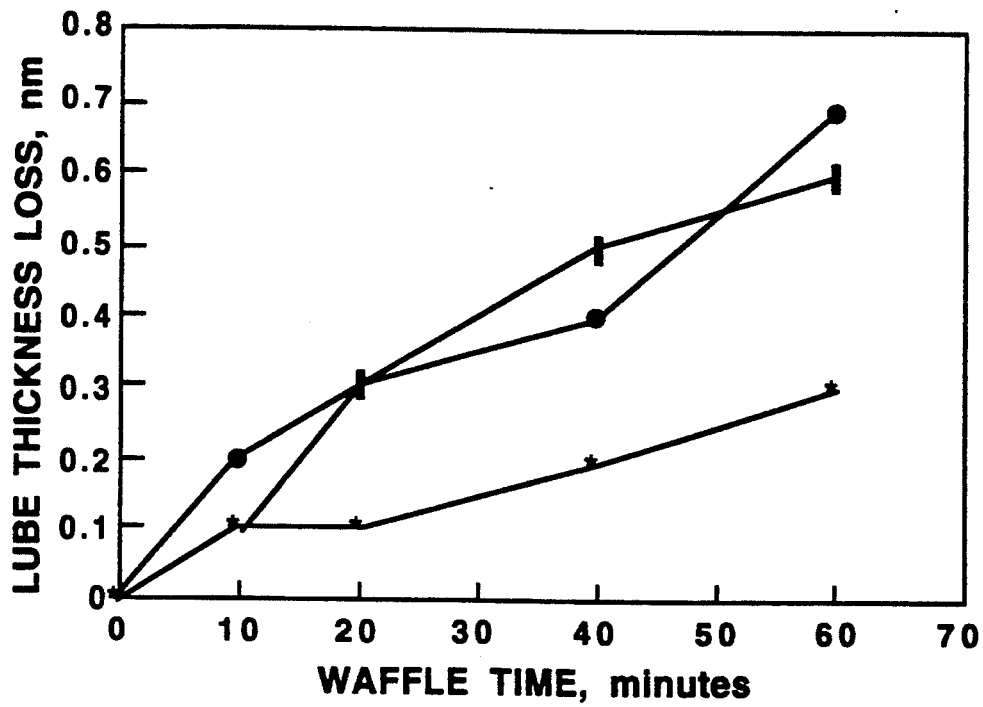
FIGS. 6A and 6B plot the loss of lubricant thickness, as a function of surface-treatment time with a waffle head (6A) or burnishing tape (6B), of a lubricated carbon overcoat formed by sputtering under pure argon (dots), argon and methane (+), argon, methane, and nitrogen (*)
Figure 6B:
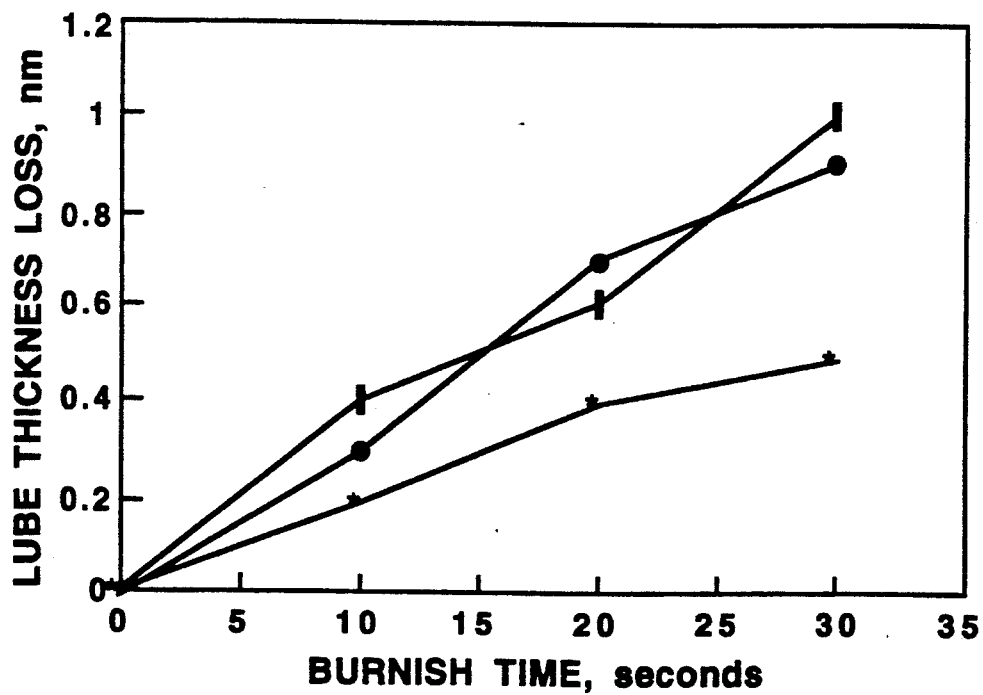

Another measure of lubricant adhesion to the overcoat is its resistance to removal by waffling or burnishing. FIG. 6A shows the loss of lubricant thickness plotted as a function of waffle time, for overcoats exposed to up to one hour time with a conventional thin-film waffle-pattern head, applied at a pressure of 9.5 g, against a lubricated disc rotating at 167 inch per seconds (IPS). The high-adhesion overcoat formed under nitrogen atmosphere (*) showed about a 3 Å loss over one hour waffling, compared with a 6–7 Å loss on overcoats formed under argon alone (solid circles) or an argon/methane mixture (+).

Similar results were obtained when discs formed with the same three overcoats were burnished by contact with an abrasive tape on a roller, as described above for surface erosion. The tape contained a 0.3μ particle abrasive, and was applied with a pressure of about 1.4 lb to the disc surface, at a disc speed of about 100 rpm.

Corrosion Resistance

One of the advantageous properties of the carbon over-coat described in the co-pending patent application is enhanced resistance to erosion. This can be seen in FIG. 8 which shows the percent corrosion, as measured by number of read-write errors in a thin-film disc, after exposure of a thin-film medium with a 300 Å overcoat. Negligible error increase was seen in the disc with a carbon overcoat formed under argon/methane (a-C:H), in contrast to an overcoat formed under pure argon, which showed a 20% increase in errors.

Figure 8:
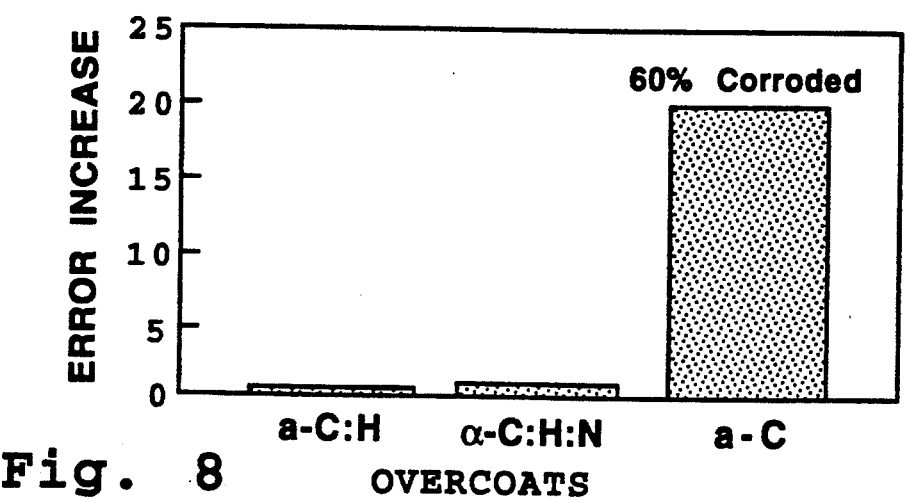
FIG. 8 is bar graph showing resistance to corrosion, as measured by error increase, in a lubricated carbon overcoat formed by sputtering under pure argon (a-C), argon and methane (a-C:H), and argon, methane, and nitrogen (a-C:H:N).

It was therefore of interest to determine if the high resistance to corrosion was preserved in a nitrogen-containing overcoat formed in accordance with the invention. As seen in FIG. 8, the degree of corrosion observed in this overcoat (a-C:H:N) was only slightly greater than in the high-resistant overcoat formed under argon/methane.

From the foregoing, it can be appreciated how various objects and features of the invention are met. The nitrogen-containing overcoat of the invention can be formed under selected voltage and pressure conditions which yield enhanced lubricity and resistance to erosion, and high corrosion resistance. These features enhance durability and the start/stop lifetime in a thin-film medium. At the same time, disc lifetime and performance is increased by the greater lubricant adhesion to the overcoat.

Although the invention has been described with respect to preferred sputtering methods, thin-film media, and methods of testing the media, it will be appreciated that various changes and modifications may be made without departing from the invention.

It is claimed:

1. A thin film magnetic medium comprising
a substrate disc,
a magnetic thin-film formed on the substrate disc, and formed on the magnetic thin-film, a carbon overcoat having a thickness less than about 500 Å, and characterized by (i) a nitrogen (1s) electron principle binding energy, as determined by electron spectrosopy for chemical analysis (ESCA), of about 399.4 eV, and (ii) a carbon structure, characterized by a carbon (1s) principle binding energy of about 284.8 eV, and oxygen atoms having an oxygen (1s) principle binding energy of about 532.5 eV, also as determined by ESCA.

2. The medium of claim 1, wherein the carbon overcoat has an oxygen abundance of no more than about 10 atom percent, as determined by ESCA.

3. The medium of claim 2, wherein the carbon overcoat includes at least about 2 atom percent nitrogen atoms, and which further includes a layer of perfluoropolyether lubricant film on the carbon overcoat.

4. An article comprising
a substrate; and
formed on the substrate, a carbon overcoat having (i) surface nitrogen atoms characterized by a nitrogen (1s) electron principle binding energy, as determined by electron spectrosopy for chemical analysis (ESCA), of about 399.4 eV, and (ii) a carbon structure characterized by a carbon (1s) principle binding energy of about 284.8 eV, and (iii) oxygen atoms having an oxygen (1s) principle binding energy of about 532.5 eV, also as determined by ESCA.

5. The article of claim 4, wherein the carbon overcoat has a thickness of less than about 500 Å, and contains at least about 2 atom percent surface nitrogen atoms.

6. The article of claim 4, wherein the carbon overcoat has an oxygen abundance of no more than about 10 atom percent.

7. The article of claim 6, which further includes a layer of perfluoropolyether lubricant film on the carbon overcoat.

8. The article of claim 7, wherein the lubricant film has a thickness of between about 15–40 Å.

* * * * *